(12) United States Patent
Schrier et al.

(10) Patent No.: US 9,315,814 B2
(45) Date of Patent: Apr. 19, 2016

(54) IMMUNOSTIMULATORY OLIGODEOXYNUCLEOTIDES

(75) Inventors: Carla Christina Schrier, Boxmeer (NL); Simon Ilg, Nieder-Olm (DE)

(73) Assignee: Intervet Inc., Madison, NJ (US)

( * ) Notice: Subject to any disclaimer, the term of this patent is extended or adjusted under 35 U.S.C. 154(b) by 4 days.

(21) Appl. No.: 14/119,492

(22) PCT Filed: May 25, 2012

(86) PCT No.: PCT/EP2012/059800
§ 371 (c)(1),
(2), (4) Date: Nov. 22, 2013

(87) PCT Pub. No.: WO2012/160184
PCT Pub. Date: Nov. 29, 2012

(65) Prior Publication Data
US 2014/0193457 A1    Jul. 10, 2014

Related U.S. Application Data

(60) Provisional application No. 61/490,387, filed on May 26, 2011.

(30) Foreign Application Priority Data

May 26, 2011  (EP) ..................... 11167605

(51) Int. Cl.
*C12N 15/117*    (2010.01)
*C12Q 1/68*    (2006.01)

(52) U.S. Cl.
CPC .......... *C12N 15/117* (2013.01); *C12N 2310/17* (2013.01); *C12N 2310/315* (2013.01); *C12N 2310/341* (2013.01); *C12N 2310/3513* (2013.01)

(58) Field of Classification Search
None
See application file for complete search history.

(56) References Cited

U.S. PATENT DOCUMENTS

| | | | |
|---|---|---|---|
| 2003/0212028 A1* | 11/2003 | Raz et al. .................... | 514/44 |
| 2004/0235774 A1 | 11/2004 | Bratzler et al. | |
| 2009/0123467 A1* | 5/2009 | Bedi et al. .................. | 424/134.1 |
| 2009/0253134 A1 | 10/2009 | Brunner et al. | |
| 2010/0003288 A1* | 1/2010 | Chaung et al. ............ | 424/278.1 |
| 2014/0193457 A1* | 7/2014 | Schrier et al. ............. | 424/204.1 |

FOREIGN PATENT DOCUMENTS

| | | |
|---|---|---|
| JP | 2005517632 | 6/2005 |
| JP | 2009542236 | 12/2009 |
| JP | 2010535248 | 11/2010 |
| WO | 2004/005476 A2 | 1/2004 |
| WO | 2004/058179 A2 | 7/2004 |
| WO | WO2006079291 A1 | 8/2006 |
| WO | WO2007020017 A1 | 2/2007 |
| WO | WO2010021289 A1 | 2/2010 |
| WO | WO2010067286 A2 | 6/2010 |
| WO | 2012/089800 A1 | 7/2012 |

OTHER PUBLICATIONS

Sequence alignment of SEQ ID No. 1 with 13976121 SEQ ID No. 1, filed Jun. 26, 2013.*
Sequence alignment of SEQ ID No. 1 with 14119514 SEQ ID No. 1, filed Nov. 22, 2013.*
Weiner et al. (PNAS. 1997; 94: 10833-10837).*
Domeika et al. (Veterinary Immunology and Immunopathology. 2004; 101: 87-102).*
Kojima et al. (Vaccine. 2002; 20: 2857-2865).*
European Search Report for 11167605.2, mailed on Nov. 8, 2011, 8 pages.
International Search Report for PCT/EP2012/059800, mailed on Aug. 28, 2012, 15 pages.
Barjesteh, Neda et al., TLR Ligands induce antiviral responses in Chicken Macrophages, Plos One, 2014, pp. 1-11 e105713, 9(8), www.plosone.org.
Burger-Kentischer, A. et al., A new cell-based innate immune receptor assay for the examination of receptor activity, ligand specificity, signalling pathways and the detection of pyrogens, Journal of Immunological Methods, Jun. 1, 2010, pp. 93-103, vol. 358, No. 1-2.
Dalpke, A. et al., Activation of toll-like receptor 9 by DNA from different bacterial species, Infection and Immunity, Feb. 2006, pp. 940-946, 74, No. 2.
Dar et al., Immunotherapeutic potential of CpG oligonucleotides in chickens, Japan Poultry Science Association, 2009, pp. 69-80, vol. 46.
Brownlie, et al., "Chicken TLR21 acts as a functional homologue to mammalian TLR9 in the recognition of CpG oligodeoxynucleotides", Molecular Immunology, 2009, pp. 3163-3170, vol. 46.
Han, et al., "Involvement of TLR21 in baculovirus-induced interleukin-12 gene expression in avian macrophage-like cell line HD11", Veterinary Microbiology, 2010, pp. 75-81, vol. 144.
Keestra, et al., "Chicken TLR 21 is an Innate CpG DNA Receptor Distinct from Mammalian TLR9", The Journal of Immunology, 2010. pp. 460-467, vol. 185.
Linghua, et al., "Vaccination with Newcastle disease vaccine and CpG oligodeoxynucleotides induces specific immunity and protection against Newcastle disease virus in SPF chicken", Veterinary Immunology and Immunopathology, 2007, pp. 216-222, vol. 115.
Rankin et al., "CpG Motif Identification for Veterinary and Laboratory Species Demonstrates That Sequence Recognition is Highly Conserved", Antisense & Nucleic Acid Drug Development, 2001, pp. 333-340, vol. 11.
European Search Report for corresponding EP Application No. EP 11 16 7605, dated Oct. 27, 2011.
PCT International Search Report for corresponding PCT International Search Report for PCT/EP2012/059800, mailed on Aug. 28, 2012.

\* cited by examiner

*Primary Examiner* — Shanon A Foley

(57) ABSTRACT

The present invention relates to immunostimulatory oligodeoxynucleotides, vectors and vaccines comprising such oligodeoxynucleotides, to their use as a medicament, to their use in preventing or combating infectious disease and to methods for the detection of such oligodeoxynucleotides.

13 Claims, 6 Drawing Sheets

SEQUENCE LISTING

```
<160> NUMBER OF SEQ ID NOS: 19

<210> SEQ ID NO 1
<211> LENGTH: 33
<212> TYPE: DNA
<213> ORGANISM: Artificial Sequence
<220> FEATURE:
<223> OTHER INFORMATION: synthetic DNA

<400> SEQUENCE: 1
gaagcttacc atgatggaga cagcggagaa ggc                                33

<210> SEQ ID NO 2
<211> LENGTH: 33
<212> TYPE: DNA
<213> ORGANISM: Artificial Sequence
<220> FEATURE:
<223> OTHER INFORMATION: synthetic DNA

<400> SEQUENCE: 2
ggcggccgct acatctgttt gtctccttcc ctg                                33

<210> SEQ ID NO 3
<211> LENGTH: 2935
<212> TYPE: DNA
<213> ORGANISM: Artificial Sequence
<220> FEATURE:
<223> OTHER INFORMATION: synthetic DNA

<400> SEQUENCE: 3
aagcttacca tgatggagac agcggagaag gcatggccca gcaccaggat gtgccctcc     60 cactgctgtc cactctggct gctgctgctg gtgacagtga cactgatgcc gatggtgcac   120
ccgtatggct ttcgcaactg cattgaggat gtcaaggcac ctttgtactt ccgctgcatc   180
cagcgcttcc tgcagtcgcc ggccctggca gtgtctgacc tgccaccaca tgccatcgcg   240
ctcaatctgt catacaacaa aatgcgctgc ctgcagccct ctgcctttgc ccacctgaca   300
cagctgcata ccctggacct gacctacaac ctcctggaga ccctctcccc tggtgccttc   360
aatgggctgg tgtgctggt ggtgctggac ctgtctcaca caagctgac cacacttgct    420 gaagggtgt tcaacagctt gggcaacctg tcctcgctgc aggtacaaca taaccccctc   480
agcacggtgt caccaagtgc tctgctaccc ctggtcaacc tgcgccgcct gtctctacgg   540
ggcgggcggc tgaatgggtt gggggcagtg gcagtggcag tgcagggctt ggcacagctg   600
gagctgttgg acctatgtga aaacaacctg acaacgctgg ggccaggccc accgctaccc   660
gcctcgctgc tcacccctgca gctgtgcaac aactcgctga gggagttagc gggggggcagc   720 ccggagatgc tatggcacgt gaagatactc gacctctcct acaacagtat ctcacaggcg   780
gaggtcttca cccagctcca cctgcgcaac atcagcctgc tccacctgat cggcaaccc    840 ttggatgtct tccacctgtt ggacatctct gacatccaac ctcgcagcct ggatttctct    900
gggttggtgc tggggctca ggggctggat aaggtgtgcc tgaggctgca gggtcccag    960
```

```
gccttgcggc ggctgcagct acaacgcaac gggctgaagg tgctgcattg taatgcactg    1020
cagttgtgtc ctgtgctgag agagctggac ctgtcctgga accggctaca gcacgtgggc    1080
tgtgccggcc ggctgctggg caagaagcag cgggagaagc tggaagtgct gacagtggaa    1140
cacaacctgc tgaagaaact gccgtcttgc ctggggggccc aggtgctgcc tcggctgtac    1200
aacatttcct tccgctttaa ccgcatcctg actgttgggc cccaagcctt tgcctacgcc    1260
ccggccctgc aggtgttgtg gctcaatatt aacagcctgg tgtggctgga caggcaggca    1320
ctgtggaggc tgcacaacct gacagagctg cgcctggaca caacctgct gaccgacctc     1380 tatcacaact ccttcattga cctccacaga ctgcgcaccc tcaacctgcg caacaaccgt    1440
gtctccgtcc tcttctctgg tgtcttccag gggctggctg agctgcagac gctggattta    1500 ggggcaaca acttgcgcca cctgactgca cagtcactgc aggggctgcc caaactgcgc    1560
aggctgtacc tggaccgcaa cagattgctg gaggtgagca gcactgtgtt cgccccagtg    1620
caggctaccc tgggggtgct ggacctgcgg gccaacaacc tgcagtacat ctcacagtgg    1680
ctgcgcaagc cgccacccett ccgcaacctg agcagcctgt acgacctgaa gctgcaggcg    1740
cagcagccct atggactgaa gatgctgcct cactacttct ccagggcttt ggtgaggctg    1800
cagcagctgt cgctgtcaca gaacatgctg cggtccatcc caccggatgt cttcgaggac    1860
ttgggccagc tgcgctccct ggcattggct gacagcagca atgggctgca tgacctgcct    1920
gacggcatct tcagaaacct gggcaacctg cggttcctgg acctggagaa tgcagggctg    1980
cactcgctca ctctggaagt cttcggcaat tcagccggc tgcaggtgct gcacttggcc      2040
agaaacgagc tgaagacctt caatgacagc gttgccagcc ggctgtcctc cttgcgctac    2100
ctggacctgc gcaagtgtcc gctcagctgc acctgtgaca catgtggct gcagggctgg     2160 ctgaacaaca gccgtgtgca ggttgtctac ccctacaact acacctgtgg ctcacagcac    2220
aatgcctaca tccacagctt tgacacacac gtctgcttcc tggacctggg gctctatctc    2280
tttgctggga ctgcaccggc agtgctgctg ctgctggtgg tgccggtggt gtaccaccgc    2340
gcctactgga ggctgaagta ccactggtac cttctgcggt gctgggtcaa ccagcggtgg    2400 cggcggggagg aaaagtgcta cctctatgac agctttgtgt cctacaattc agctgatgaa    2460
agttgggtgt gcagaagct ggtgcctgag ctggagcacg gtgccttccg cctctgcttg     2520
caccaccgcg acttccagcc gggccgcagc atcattgaca acattgtgga tgctgtctac    2580
aacagccgga agacggtgtg cgtggtgagc cgcagctacc tgcgcagcga gtggtgctct    2640
ctagaggtgc agttggccag ctaccggctg ttggatgagc ggcgtgacat cctggtactg    2700
gtgctgctgg aggacgtggg tgatgctgag ctgtctgcct accaccgcat gcggcgggtg    2760
ctgctgcggc gcacctacct gcgctggcct cttgaccccg cagctcagcc gctcttttgg    2820
gcacggctga gagggcact gaggtgggga gaggaggag aggaggagga agaagaaggt      2880
ttgggtggag ggacgggaag gcccagggaa ggagacaaac agatgtagcg gccgc         2935
```

<210> SEQ ID NO 4
<211> LENGTH: 22
<212> TYPE: DNA
<213> ORGANISM: Artificial Sequence
<220> FEATURE:
<223> OTHER INFORMATION: synthetic DNA

<400> SEQUENCE: 4

```
ggggggggtcg tcgtcgtcgt cg                                               22
```

```
<210> SEQ ID NO 5
<211> LENGTH: 28
<212> TYPE: DNA
<213> ORGANISM: Artificial Sequence
<220> FEATURE:
<223> OTHER INFORMATION: synthetic DNA

<400> SEQUENCE: 5 ggggggtcg tcgtcgtcgt cgtcgtcg                                        28

<210> SEQ ID NO 6
<211> LENGTH: 34
<212> TYPE: DNA
<213> ORGANISM: Artificial Sequence
<220> FEATURE:
<223> OTHER INFORMATION: synthetic DNA

<400> SEQUENCE: 6 ggggggtcg tcgtcgtcgt cgtcgtcgtc gtcg                                 34

<210> SEQ ID NO 7
<211> LENGTH: 40
<212> TYPE: DNA
<213> ORGANISM: Artificial Sequence
<220> FEATURE:
<223> OTHER INFORMATION: synthetic DNA

<400> SEQUENCE: 7 ggggggtcg tcgtcgtcgt cgtcgtcgtc gtcgtcgtcg                           40

<210> SEQ ID NO 8
<211> LENGTH: 46
<212> TYPE: DNA
<213> ORGANISM: Artificial Sequence
<220> FEATURE:
<223> OTHER INFORMATION: synthetic DNA

<400> SEQUENCE: 8 ggggggtcg tcgtcgtcgt cgtcgtcgtc gtcgtcgtcg tcgtcg                    46

<210> SEQ ID NO 9
<211> LENGTH: 52
<212> TYPE: DNA
<213> ORGANISM: Artificial Sequence
<220> FEATURE:
<223> OTHER INFORMATION: synthetic DNA

<400> SEQUENCE: 9 ggggggtcg tcgtcgtcgt cgtcgtcgtc gtcgtcgtcg tcgtcgtcgt cg             52

<210> SEQ ID NO 10
<211> LENGTH: 58
<212> TYPE: DNA
<213> ORGANISM: Artificial Sequence
<220> FEATURE:
<223> OTHER INFORMATION: synthetic DNA

<400> SEQUENCE: 10 ggggggtcg tcgtcgtcgt cgtcgtcgtc gtcgtcgtcg tcgtcgtcgt cgtcgtcg       58

<210> SEQ ID NO 11
<211> LENGTH: 64
<212> TYPE: DNA
<213> ORGANISM: Artificial Sequence
<220> FEATURE:
<223> OTHER INFORMATION: synthetic DNA
```

<400> SEQUENCE: 11
gggggggtcg tcgtcgtcgt cgtcgtcgtc gtcgtcgtcg tcgtcgtcgt cgtcgtcgtc    60
gtcg                                                                 64

<210> SEQ ID NO 12
<211> LENGTH: 70
<212> TYPE: DNA
<213> ORGANISM: Artificial Sequence
<220> FEATURE:
<223> OTHER INFORMATION: synthetic DNA

<400> SEQUENCE: 12
gggggggtcg tcgtcgtcgt cgtcgtcgtc gtcgtcgtcg tcgtcgtcgt cgtcgtcgtc    60
gtcgtcgtcg                                                           70

<210> SEQ ID NO 13
<211> LENGTH: 76
<212> TYPE: DNA
<213> ORGANISM: Artificial Sequence
<220> FEATURE:
<223> OTHER INFORMATION: synthetic DNA

<400> SEQUENCE: 13
gggggggtcg tcgtcgtcgt cgtcgtcgtc gtcgtcgtcg tcgtcgtcgt cgtcgtcgtc    60
gtcgtcgtcg tcgtcg                                                    76

<210> SEQ ID NO 14
<211> LENGTH: 82
<212> TYPE: DNA
<213> ORGANISM: Artificial Sequence
<220> FEATURE:
<223> OTHER INFORMATION: synthetic DNA

<400> SEQUENCE: 14
gggggggtcg tcgtcgtcgt cgtcgtcgtc gtcgtcgtcg tcgtcgtcgt cgtcgtcgtc    60
gtcgtcgtcg tcgtcgtcgt cg                                             82

<210> SEQ ID NO 15
<211> LENGTH: 88
<212> TYPE: DNA
<213> ORGANISM: Artificial Sequence
<220> FEATURE:
<223> OTHER INFORMATION: synthetic DNA

<400> SEQUENCE: 15
gggggggtcg tcgtcgtcgt cgtcgtcgtc gtcgtcgtcg tcgtcgtcgt cgtcgtcgtc    60
gtcgtcgtcg tcgtcgtcgt cgtcgtcg                                       88

<210> SEQ ID NO 16
<211> LENGTH: 28
<212> TYPE: DNA
<213> ORGANISM: Artificial Sequence
<220> FEATURE:
<223> OTHER INFORMATION: synthetic DNA

<400> SEQUENCE: 16
ggggggtcgt cgtcgtcgtc gtcggggg                                       28

<210> SEQ ID NO 17
<211> LENGTH: 41
<212> TYPE: DNA
<213> ORGANISM: Artificial Sequence

```
<220> FEATURE:
<223> OTHER INFORMATION: synthetic DNA

<400> SEQUENCE: 17 gggggggttcg ttttcgtttt cgttttcgtt ttcgttgggg g           41

<210> SEQ ID NO 18
<211> LENGTH: 36
<212> TYPE: DNA
<213> ORGANISM: Artificial Sequence
<220> FEATURE:
<223> OTHER INFORMATION: synthetic DNA

<400> SEQUENCE: 18
gggggtcgtc gtcgtcgtcg tcgtcgtcgt cggggg                  36

<210> SEQ ID NO 19
<211> LENGTH: 32
<212> TYPE: DNA
<213> ORGANISM: Artificial Sequence
<220> FEATURE:
<223> OTHER INFORMATION: synthetic DNA

<400> SEQUENCE: 19
gggggtcgtc gtcgtcgtcg tcgtcgtcgt cg                      32
```

IMMUNOSTIMULATORY OLIGODEOXYNUCLEOTIDES

CROSS-REFERENCE TO RELATED APPLICATIONS

Figure 1:
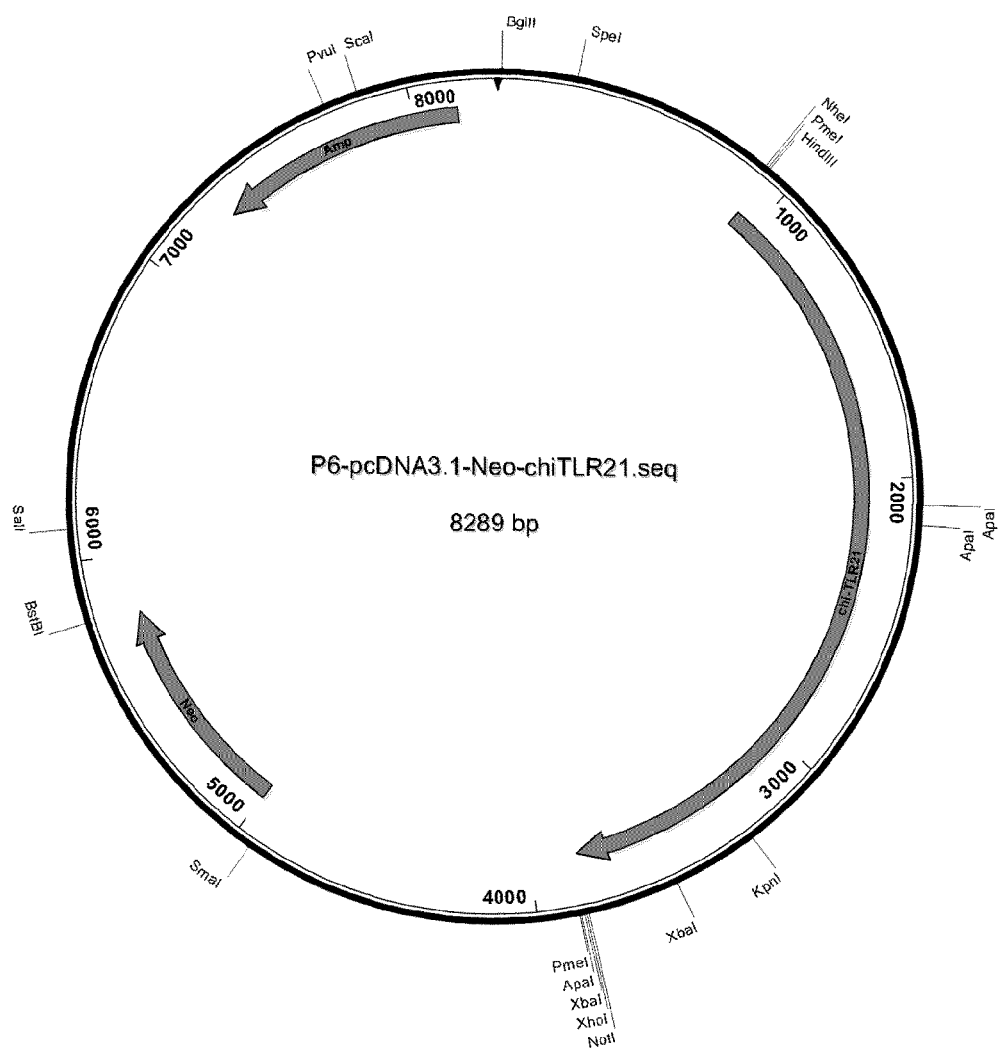
Figure 2:
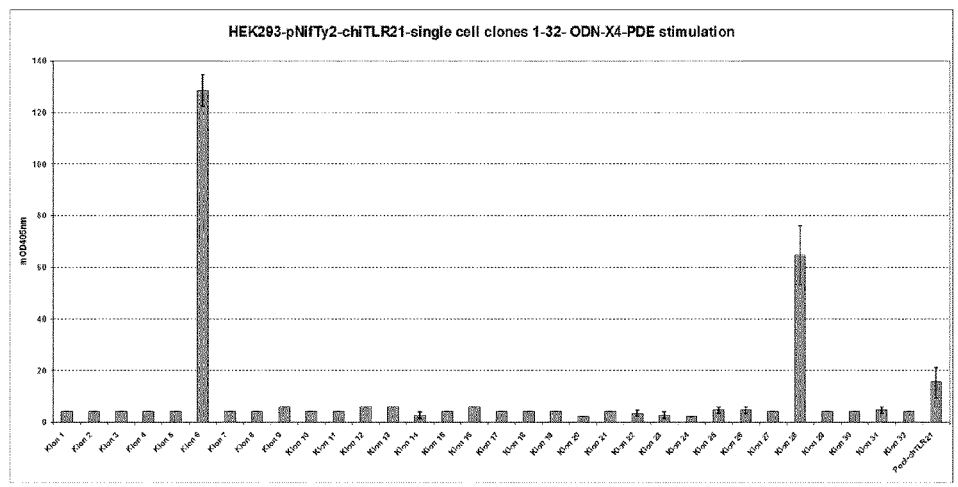
Figure 3:
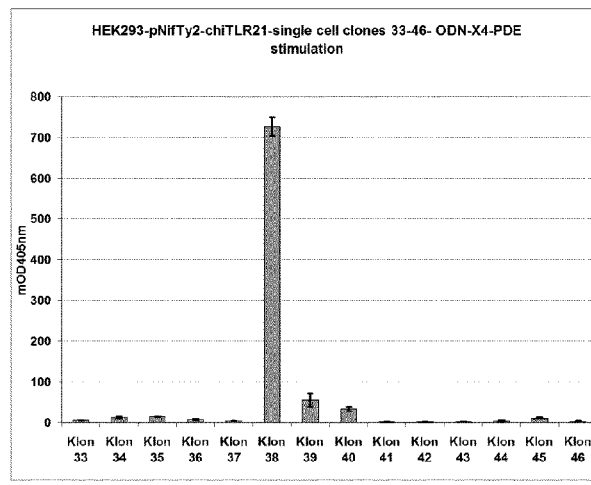
Figure 4:
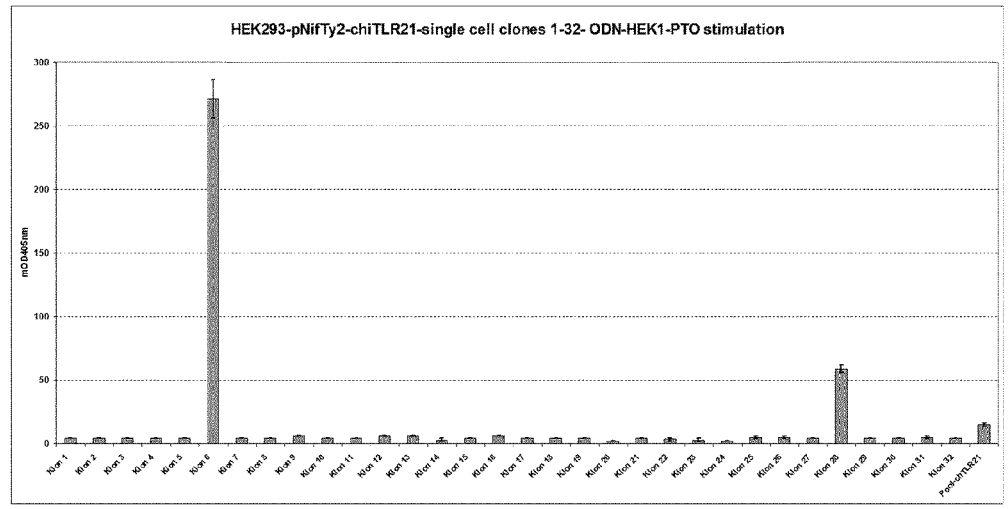
Figure 5:
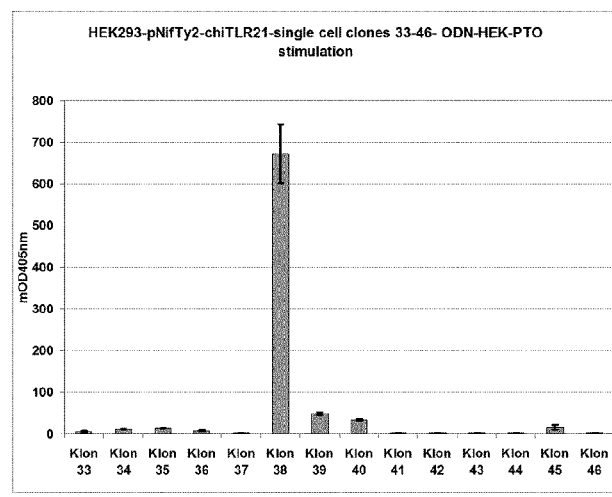

This application is a national stage entry under 35 U.S.C. §371 of PCT/EP2012/059800, filed on May 25, 2012, which claims priority to U.S. Provisional Application No. 61/490,387 filed on May 26, 2011, and EP Application No. 11167605.2, filed on May 26, 2011. The content of PCT/EP2012/059800 is hereby incorporated by reference in its entirety.

The present invention relates to immunostimulatory oligodeoxynucleotides, vectors and vaccines comprising such oligodeoxynucleotides, to their use as a medicament, to their use in preventing or combating infectious disease and to methods for the detection of such oligodeoxynucleotides.

During the past two decades, it has emerged in immunological science that the vertebrate immune system possesses mechanisms to detect microbial infection and to trigger rapid immune activation via the receptor-mediated recognition of unique characteristics of pathogens, the so-called pathogen-associated molecular patterns (PAMPs) interacting with cognate host pathogen recognition receptors (PRRs) (Iwasaki A, Medzhitov R. 2001. *Science* 327, 291-295. Medzhitov R., 2009. *Immunity* 30, 766-775).

It is now clear that certain forms of pathogen deoxyribonucleic acid (DNA) are amongst these PAMPs. In 1995 it was reported that non-methylated CpG motifs in bacterial DNA trigger murine B-cell activation (Krieg et al. 1995). This study generated for the first time a link between the specific recognition of bacterial immunostimulatory non-methylated CpG-containing DNA and the previously recognized CpG suppression as well as the widespread CpG methylation in mammalian DNA. The most effective B cell stimulatory non-methylated CpG oligodeoxynucleotide (CpG ODN) was shown to possess the sequence element GACGTT.

The next landmark paper in the field was published by Shizuo Akira's laboratory in Osaka/Japan (Hemmi et al. 2000). By a gene cloning and a targeted gene knockout approach in mice it could be unequivocally shown, that the cellular response in mice to CpG-ODNs is mediated by the toll-like receptor 9 (TLR9). Subsequently it was shown that the CpG-ODNs are agonists for TLR9 signaling predominantly via the NF kappa-B pathway (Medzhitov 2001). In the following decade, quite a number of studies have been published on basic research topics and on general potential immunotherapeutic applications (e. g. reviewed in Krieg 2002, 2003, 2006; Klinman 2004, Vollmer 2005, Wilson et al. 2006, Kindrachuk et al. 2008, Dorn and Kippenberger 2008, Vollmer and Krieg 2009, Wilson et al. 2009). A number of review articles focus on anti-infective applications of CpG-ODNs (Krieg 2007), the use of TLR9 agonists in the treatment of cancer (Krieg 2007, Weiner 2009), TLR9 activation for asthma and allergy treatment (Kline 2007, Kline and Krieg 2008, Fonseca and Kline 2009) and as vaccine adjuvants (Klinman et al. 2004, Klinman 2006, Daubenberger 2007, Wagner 2009, Mutwiri et al. 2009, Klinman et al. 2009).

CpG ODNs have also been described and discussed as immunostimulatory agents and vaccine adjuvants in veterinary applications, particularly in bovines, pigs, sheep, dogs, chicken and fish (Babiuk et al. 2003, Carrington and Secombes 2006, Griebel et al. 2005, Mutwiri et al. 2003, Singh and O'Hagan 2003, Werling and Jungi 2003).

In the field of veterinary uses in chickens, the use of CpG oligodeoxynucleotides in e.g. vaccines to protect chickens against Newcastle Disease has been described (Linghua 2007). It has recently been shown that in chicken, TLR21 acts as a functional homologue to mammalian TLR9 in the recognition of CpG oligodeoxynucleotides (Brownlie et al., 2009).

The design of specific CpG ODN's as immunomodulators has so far been quite random. This is especially true for non-mammalian CpG ODN's. The reason for this is multi-factorial; first of all there is no knowledge about correlation between immuno modulatory CpG motifs for human TLR's and for TLR's in non-human, let alone non-mammalian species. Secondly, there are no cell-systems available with a sufficiently low background to noise level to selectively test the effects of very low concentrations of CpG ODN's. Moreover, there are no high-throughput screening methods available and even if there were, there is no clear correlation between in vivo versus in vitro efficacy of CpG ODN's as immuno-modulators in non-mammalian species.

Thus, there clearly is a need for novel CpG ODN's that have a high immuno-modulatory effect and therefore are effective in low doses. And there is a need for selective and sensitive CpG ODN selection systems for veterinary purposes that show a correlation between in vitro and in vivo activity of CpG-activity.

It is one of the objectives of the present invention to provide such novel CpG ODN's.

In this respect, one embodiment of the present invention relates to an immunostimulatory non-methylated oligodeoxynucleotide having the general formula $$5'[G]_x\{TCGTCG\}_n TCG[G]_z 3'$$

wherein n=2-100, x=3-20 and z=0-10, and pharmaceutically acceptable salts thereof.

An "immunostimulatory non-methylated oligodeoxynucleotide" refers to an oligodeoxynucleotide, which contains a non-methylated cytidine-phosphate-guanosine di-nucleotide sequence that stimulates the initiation of signaling cascades leading to activation of transcription factors such as NF-κB or Interferon Regulatory Factor 3 (IRF3). It is this activation that in turn results in the expression of inflammatory cytokines and other cellular activation events. NF-κB binding sites and gene expression influenced by NF-κB are i.a. described by Schindler and Baichwal (1994).

The term oligodeoxynucleotide means a short nucleic acid polymer of deoxynucleotides; i.e. a molecule comprising a multitude of deoxyriboses, linked to a phosphate group and to an exchangeable organic base. Such an organic base is a substituted pyrimidine or a substituted purine. Examples are cytosine and thymine respectively adenine and guanine.

The oligonucleotides according to the invention may comprise modifications. Examples of such modifications are e.g. modifications in the phosphodiester internucleoside bridge located at the 3' and/or 5' end of a nucleoside. Such modifications relate i.a. to the replacement of a phosphodiester by e.g. a phosphorothioate or a phosphorodithioate.

Other modifications are e.g. replacements of a phosphodiester bridge by a dephospho bridge. Examples of dephospho bridges are methylhydroxylamine, formacetal and dimethylenesulfone groups.

Still other modifications are modifications that concern the replacement of a natural nucleoside base by a non-natural nucleoside base such as inosine, 5-fluorocytosine, 7-deaza-7-substituted guanine, 7-deaza-8-substituted guanine, 2-thiouracil, dihydrouracil, 5-bromo-cytosine, 6-substituted cytosines, N4-substituted cytosines, Again other modifications are modifications concerning the replacement of a sugar unit; a β-ribose sugar or a β-D-2'-ribose sugar unit by a modified sugar unit such as e.g. an L-2'-deoxyribose or 2'-L-arabinose.

A text book giving further insight in oligonucleotides is e.g. "PCR Primer: A Laboratory Manual", Second Edition, 2003, Edited By Carl W. Dieffenbach, *National Institute of Allergy and Infectious Diseases*; Gabriela S. Dreksler, *Uniformed Services University of the Health Sciences*, Cold Spring Harbor Laboratory Press ISBN 978-087969654-2.

The structure $^{5'}\{TCGTCG\}_n^{3'}$ carrying the CpG motif represents the active immunostimulating moiety of an ODN according to the invention. Therefore, the present invention provides immunostimulatory oligodeoxynucleotides that comprise this so-called "backbone".

It was found that the backbone of an oligodeoxynucleotide according to the invention, the structure $^{5'}\{TCGTCG\}_n^{3'}$ must be present at least two, preferably three times. Therefore, n should be at least two. It was also found that the activity of the oligodeoxynucleotides increases when n increases. This effect is leveling when n increases. Basically, the number n of the backbone structure should therefore be at least 2. Preferably, the range of n is $3 \leq n \leq 100$, merely because of the fact that the longer the synthetic sequence the more difficult it is to make. In practice preferably the range of n is $3 \leq n \leq 18$. More preferably, the range of n is $4 \leq n \leq 18$, even more preferably the range of n is $5 \leq n \leq 18$, still even more preferably the range of n is $6 \leq n \leq 18$.

The identification of CpG ODN's according to the invention was made possible i.a. by using a more selective detection system than the systems currently in use for the detection of NF-κB activation. Brownlie at al. (2009) describe an NF-κB luciferase based reporter system. Other systems are e.g. based upon IL-8 transcript measurement or cytokine secretion or the detection of NO secretion.

Contrary to this, in the present invention a secreted alkaline phosphatase based detection system (SEAP) was used. SEAP is a reporter enzyme in mammalian systems (Yang et al., 1997). This system turned out to be surprisingly sensitive and in addition surprisingly provides a close correlation between the in vitro and in vivo activities of the CpG ODN's tested. The SEAP system was used with para-nitrophenylphosphate (pNPP) as a substrate.

Another improvement over existing systems was the introduction and stable maintenance in cells of the plasmid carrying the SEAP gene. Up till now, all detection systems used transient transfection of cells with the reporter gene. It is due to the introduction and stable maintenance in cells of the reporter gene that now for the first time a dose/response curve could be made. Such a curve is essential if a reliable comparison between various CpG ODN's activity is to be made.

Therefore, the methods and cell lines described in detail in the Examples section of the present invention allow for the first time to make a reliable side-by-side comparison between various CpG ODN's.

Further details of the system used are given in the Examples section.

It was found that an increase in the number of G's at the 5'-end of the structure $^{5'}[G]_x\{TCGTCG\}_n TCG[G]_z^{3'}$ leads to an increase of the activity of the CpG ODN. The value x should preferably be at least 3, but increasing numbers of G's up to 20 G's improve the activity of the CpG ODN. Therefore more preferably, x is 4, 5, 6, 7, 8, 9, 10, 11, 12, 13, 14, 15, 16, 17, 18, 19 or 20 in that increasing order of preference.

It was also found that an increase in the number of G's ate the 3'-end of the structure $^{5'}[G]_x\{TCGTCG\}_n TCG[G]_z^{3'}$ leads to a (slight) decrease of the activity of the CpG ODN. The value z should preferably be 10 or less than 10, but decreasing numbers of G's down to 0 G's improves the activity of the CpG ODN. Therefore more preferably z is 9, 8, 7, 6, 5, 4, 3, 2, 1 or 0, in that increasing order of preference.

As said above, several kinds of modifications in the phosphodiester internucleoside bridge located at the 3' and/or 5' end of a nucleoside are feasible. But basically, depending upon the way of synthesis, usual common types of bonds between two nucleotides are: phosphodiester (PDE) bonds and phosphorothioate (PTO) bonds. In order to improve the stability and the immunostimulatory effect of CpG ODN's, the building blocks of synthetic oligodeoxynucleotides are usually provided with phosphorothioates, so that they form PTO bonds.

It was surprisingly found, however, that when only the $^{5'}[G]_x$ and the $^{3'}[G]_x$ nucleotides are bound by PTO bonds and the other nucleotides are bound by PDE bonds, the efficacy of the oligodeoxynucleotide according to the invention is further increased. (In such cases, the $^{5'}[G]_x$ to $\{TCGTCG\}_n TCG[G]_z^{3'}$ bond is a PTO, while the $^{5'}[G]_x\{TCGTCG\}_n TCG$ to $[G]_z^{3'}$ bond is a PDE.)

Therefore, another preferred form of this embodiment relates to oligodeoxynucleotides according to the invention wherein the $^{5'}[G]_x$ and the $^{3'}[G]_z$ nucleotides have a phosphorothioate binding and the other nucleotides have a phosphodiester binding.

Normally, CpG oligodeoxynucleotides are active in nanomolar amounts, both in the in vitro test system and in vivo.

Surprisingly, however, the CpG oligodeoxynucleotides according to the invention are even active in picomolar (sub-nanomolar) amounts; their EC50 is below 1 nM.

The half-maximal effective concentration (EC50) of an oligodeoxynucleotide is the amount of oligodeoxynucleotide that is necessary to induce an amount of the reporter enzyme SEAP (that produces the colored product absorbing at 405 nm) in the reporter cells (HEK293-pNifty2-chickenTLR21 or HD11-pNifTy2Hyg) that gives a half-maximal enzymatic reaction rate. If the EC50 of an oligodeoxynucleotide is below 1 nM in these cells, it is considered to be active in picomolar (sub-nanomolar) amounts.

It is very well possible to link an oligodeoxynucleotide according to the invention to a carrier or hapten, via a reactive chemical group. Such linkage enhances the immunostimulatory effect of the combined molecules.

Mere examples of such components are e.g. digoxigenin, aminohexyl-, Texas red and biotin.

Preferred carriers or haptens are 3'- and 5'-labeled Texas red and 5'-labeled digoxigenin. The linkage of oligodeoxynucleotides to haptens/carriers is well-known in the art.

Another embodiment of the invention relates to a vector comprising an immunostimulatory non-methylated oligodeoxynucleotide according to the invention. Such a vector can be a nucleic acid molecule such as a plasmid, a virus, a bacteriophage or any other vector used in molecular biology. Merely as an example: a vector comprising an immunostimulatory non-methylated oligodeoxynucleotide can e.g. be a DNA molecule such as a plasmid that can be multiplied in bacteria, into which an immunostimulatory non-methylated oligodeoxynucleotide according to the invention has been cloned. Such a plasmid preferably has an active origin of replication, causing high numbers of the plasmid to be present in the host. Growing such bacteria on a large scale followed by isolation of the plasmids provides an alternative for the synthetic production of the immunostimulatory non-methylated oligodeoxynucleotide according to the invention.

One of the aims of the present invention is to provide new CpG ODN's that can be used as successful immunostimulating components in vaccines that prevent or combat infectious disease together with an antigen component or genetic information encoding an antigen component, and a pharmaceutically acceptable carrier.

In general, the term antigen component refers to a composition of matter that comprises at least one epitope that can induce, stimulate or enhance an immune response when administered to a human or an animal.

The antigen component may be any kind of antigen component but preferably is derived from a micro-organism or virus that in its wild-type form is pathogenic to humans or animals.

The antigen component can be the whole pathogen, preferably in an inactivated or attenuated form, an extract of the pathogen or an immunogenic protein of the pathogen.

If the antigen component is an immunogenic protein of the pathogen, that immunogenic protein is preferably expressed in and recovered from in vitro cultured cells.

Therefore, another embodiment relates to a vaccine for preventing or combating infectious disease characterised in that said vaccine comprises an immunostimulating amount of an oligodeoxynucleotide according to the invention and/or a vector according to the invention, an immunogenic amount of an antigen component or genetic information encoding an antigen component, and a pharmaceutically acceptable carrier.

Of course, the immunostimulating amount of the oligodeoxynucleotide and the immunogenic amount of the antigen component are strongly interrelated. It is one of the merits of the present invention that the presence of the oligodeoxynucleotide according to the invention can lower the amount of antigen component that is necessary to prevent or combat infectious disease.

The amount of antigen component that is necessary to prevent or combat infectious disease is referred to as the immunogenic amount of the antigen component.

An immunostimulating amount of the oligodeoxynucleotide is the amount that is capable of decreasing the immunogenic amount of the antigen component, i.e. the amount of the antigen component that is necessary to prevent or combat an infectious disease.

So basically, the wording "immunostimulating amount of the oligodeoxynucleotide" and "immunogenic amount" must be seen in relation to each other.

It goes without saying that, if the vaccine comprises genetic information encoding an antigen component, the amount of antigen component expressed by this genetic information should be enough to prevent or combat infectious disease, i.e.; it must be an immunogenic amount.

The fact that the non-methylated oligodeoxynucleotides according to the invention are immunostimulatory, means that they enhance the immunological efficacy of antigen components in vaccines. For that reason, vaccines according to the invention will in many cases comprise less of the antigen component or the genetic information encoding the antigen component than would be the case if no oligodeoxynucleotides according to the invention would be present.

In some cases an antigen component as such, without the addition of immunostimulatory oligonucleotides, may have such low immunogenic properties that high amounts must be given anyway, albeit without reaching the desired immunogenic level. In such cases, the antigen component can be given in the usual high concentration, however now together with an oligodeoxynucleotide according to the invention in order to so obtain the desired level of immunogenicity.

Thus, the amount of the antigen component or the genetic information encoding the antigen component to be administered with a oligonucleotide according to the invention would as a rule of thumb be equal or below the amount given in the absence of the oligonucleotide. The skilled person involved in the manufacturing of a specific vaccines, would know that amount for that specific vaccine. Also, the Examples give e.g. ample guidance for the amount of antigen components to be used, e.g. in three different inactivated viral vaccines: Newcastle disease virus vaccine, Infectious Bronchitis virus vaccine and Turkey Rhinotracheitis vaccine.

The amount of the oligodeoxynucleotide according to the invention that needs to be administered together with the antigen component or the genetic information encoding the antigen component depends both on the selected oligodeoxynucleotide and the antigen component.

A very suitable amount of oligodeoxynucleotide according to the invention would usually vary between 1 and 100 nanomol. Very good in vivo results have e.g. been obtained with 1-10 µg of oligodeoxynucleotides according to the invention with an average length of 30 deoxynucleotides that were shown to be active in in vitro tests in the nanomolar range.

If an oligodeoxynucleotide is chosen from the group of oligodeoxynucleotides that are active in the picomolar range, the skilled person would realise that amounts below, possibly far below, 1 nanomol, i.e. picomolar amounts, would be worth testing before testing nanomolar amounts.

Vaccines according to the invention comprise a pharmaceutically acceptable carrier. The nature of this carrier depends i.a. upon the route of administration. If the administration route is through the oral or intranasal route, the carrier could be as simple as sterile water, a physiological salt solution or a buffer. If injection is the preferred route, the carrier should preferably be isotonic and have pH restrictions that make it suitable for injection. Such carriers however are extensively known in the art.

Vaccines according to the invention may, in addition to the antigen component or the genetic information encoding the antigen component, and an oligodeoxynucleotide according to the invention, comprise an adjuvant. Adjuvants in general are substances that boost the immune response of the host in a non-specific manner.

Many adjuvants are known in the art to be suitable, such as Freund's Complete and Incomplete adjuvant, vitamin E, non-ionic block polymers and poly-anions such as dextran sulphate, carbopol and pyran, alum hydroxide. Also frequently used are alum phosphate, saponins, vegetable oils such as tocopherol and mineral oils. Very efficient adjuvants are oil-in-water emulsions and especially water-in-oil emulsions, further also referred to as are oil-in-water adjuvants and water-in-oil adjuvants. Such emulsions are well-known in the art. Thus, preferably, the vaccine comprises a water-in-oil adjuvant.

Preferably the antigen component is, or is derived from a virus or micro-organism that in its wild-type form is pathogenic to poultry.

More preferably, said virus or micro-organism is selected from the group consisting of Infectious Bronchitis virus, Newcastle Disease virus, Infectious Bursal Disease (Gumboro), Chicken Anaemia agent, Avian Reovirus, *Mycoplasma gallisepticum*, Turkey Rhinotracheitis virus, *Haemophilus paragallinarum* (Coryza), Chicken Poxvirus, Avian Encephalomyelitis virus, Egg Drop syndrome virus, Infectious Laryngotracheitis virus, Herpes Virus of Turkeys, *Eime-* ria species, *Ornithobacterium rhinotracheale, Pasteurella multocida, Mycoplasma synoviae, Salmonella* species and *Escherichia coli.*

Again another embodiment of the present invention relates to an immunostimulatory non-methylated oligodeoxynucleotide according to the invention for use as a medicament Again another embodiment of the present invention relates to an immunostimulatory non-methylated oligodeoxynucleotide according to the invention for use in preventing or combating infectious disease in poultry Up till now, all detection systems used transient transfection of cells with the reporter gene. Such transient systems do not allow for a reliable side-by-side comparison of the efficacy of CpG ODN's. As said above, a major improvement over existing systems was the introduction and stable maintenance in cells, of the plasmid carrying the reporter gene. Stable means that the plasmid remains present in the cell after several cell division cycles.

Frequently, stable maintenance of a plasmid is obtained by growing the cells under the pressure of one or more selective agents, such as antibiotics for which a resistance gene is present on the plasmid. Loss of the plasmid would then cause the cell that lost the plasmid to die. Remaining viable cells would still harbour the plasmid.

Another way of stable maintenance would be transfection with linearized plasmids. Such plasmids usually become integrated in the genome of the cell, and thus be stably maintained. Thus, still another embodiment of the present invention relates to a cell comprising a TLR21-receptor and a plasmid encoding an NF-κB reporter gene, which plasmid is stably maintained in the cell. Such cells are very suitable for use in the screening of CpG molecules, more specifically the screening of CpG molecules according to the invention.

The Examples give ample guidance about how to obtain such a cell comprising a plasmid encoding a reporter gene that can be stably maintained in the cell.

As also mentioned above, detection systems based upon secreted alkaline phosphatase (SEAP) were shown to be very suitable for the detection system used.

Thus, preferably the reporter gene is a gene encoding secreted alkaline phosphatase.

Basically, any cell or cell line carrying and expressing a TLR21 that allows introduction and preferably the stable maintenance of a plasmid carrying a NF-κB reporter gene, preferably the SEAP gene as described above is suitable for testing TLR21-specific CpG ODN's.

A preferred example of such a suitable cell line for testing TLR21-specific CpG ODN's is the chicken cell line HD11.

Therefore, preferably, a cell line for use in the detection system is a HD11 cell line comprising a stable plasmid encoding a reporter gene.

Chicken cell lines such as the HD11 cell line display a whole panel of chicken-TLR's. This may in certain conditions generate a certain background activity.

Therefore, non-poultry cell lines such as mammalian cell lines are more preferred cell lines. An example of such a mammalian cell line is a HEK293 cell into which the TLR21 has been cloned. Such a cell line is more specifically selective for TLR21-activating signals.

Therefore, more preferably, a cell line for use in the detection system is the mammalian cell line HEK293 comprising a stably maintained reporter gene and into which HEK293 cell the TLR21 has been cloned.

Still another embodiment of the present invention relates to a method for the detection of immunostimulatory oligodeoxynucleotides according to the invention wherein that method comprises the steps of a) contacting an oligodeoxynucleotide with a cell according to the invention, b) detecting the level of product of the reporter gene.

In a preferred form of this method, the product of the reporter gene is SEAP

A more preferred form of this embodiment relates to a method for the detection of immunostimulatory oligodeoxynucleotides according to the invention, wherein the cell is a cell of chicken cell line HD11, or a HEK293 cell line into which chicken TLR21 has been cloned.

EXAMPLES

Example 1

Gene Cloning and Heterologous Expression of Chicken TLR21

Recent progress in chicken TLR research suggests that TLR21 is the functional homolog of mammalian TLR9 in avian species (Keestra 2008, Brownlie et al. 2009).
Outline of TLR21 Gene Cloning Based on the Genbank database sequence NM_001030558, a primer pair was synthesized for the polymerase chain reaction (PCR) amplification of the chicken TLR21 gene:
Ga-TLR21-for1
G<u>AAGCTT</u>*ACC*ATGATGGAGACAGCGGAGAAGGC
Ga-TLR21-rev1 (SEQ ID NO.:1)
GG<u>CGGCCGC</u>TACATCTGTTTGTCTCCTTCCCTG (SEQ ID NO.:2)

The primers were designed to provide flanking restriction cloning sites (underlined) and a Kozak sequence (italic) to the start and stop codons (bold). RT-PCR was performed using these primers and chicken spleen total RNA as a template. A PCR product of the expected size (~3000 bp) was cloned into pCR2.1-Topo and 5 independent plasmid clones (P1, P2, P12, P13, P14) were sequenced.

(SEQ ID NO.:3)
DNA sequence of chicken TLR21, as used.
<u>AAGCTT</u>*ACC*ATGATGGAGACAGCGGAGAAGGCATGGCCCAGCACCAGGATGTGCCCCTCCCACTGCTGTCCACTCTGGC

TGCTGCTGCTGGTGACAGTGACACTGATGCCGATGGTGCACCCGTATGGCTTTCGCAACTGCATTGAGGATGTCAAGGC

ACCTTTGTACTTCCGCTGCATCCAGCGCTTCCTGCAGTCGCCGGCCCTGGCAGTGTCTGACCTGCCACCACATGCCATC

GCGCTCAATCTGTCATACAACAAAATGCGCTGCCTGCAGCCCTCTGCCTTTGCCCACCTGACACAGCTGCATACCCTGG

ACCTGACCTACAACCTCCTGGAGACCCTCTCCCCTGGTGCCTTCAATGGGCTGGGTGTGCTGGTGGTGCTGGACCTGTC

TCACAACAAGCTGACCACACTTGCTGAAGGGGTGTTCAACAGCTTGGGCAACCTGTCCTCGCTGCAGGTACAACATAAC

CCCCTCAGCACGGTGTCACCAAGTGCTCTGCTACCCCTGGTCAACCTGCGCCGCCTGTCTCTACGGGGCGGGCGGCTGA

-continued
```
ATGGGTTGGGGGCAGTGGCAGTGGCAGTGCAGGGCTTGGCACAGCTGGAGCTGTTGGACCTATGTGAAAACAACCTGAC

AACGCTGGGGCCAGGCCCACCGCTACCCGCCTCGCTGCTCACCCTGCAGCTGTGCAACAACTCGCTGAGGGAGTTAGCG

GGGGGCAGCCCGGAGATGCTATGGCACGTGAAGATACTCGACCTCTCCTACAACAGTATCTCACAGGCGGAGGTCTTCA

CCCAGCTCCACCTGCGCAACATCAGCCTGCTCCACCTGATCGGCAACCCCTTGGATGTCTTCCACCTGTTGGACATCTC

TGACATCCAACCTCGCAGCCTGGATTTCTCTGGGTTGGTGCTGGGGGCTCAGGGGCTGGATAAGGTGTGCCTGAGGCTG

CAGGGTCCCCAGGCCTTGCGGCGGCTGCAGCTACAACGCAACGGGCTGAAGGTGCTGCATTGTAATGCACTGCAGTTGT

GTCCTGTGCTGAGAGAGCTGGACCTGTCCTGGAACCGGCTACAGCACGTGGGCTGTGCCGGCCGGCTGCTGGGCAAGAA

GCAGCGGGAGAAGCTGGAAGTGCTGACAGTGGAACACAACCTGCTGAAGAAACTGCCGTCTTGCCTGGGGGCCCAGGTG

CTGCCTCGGCTGTACAACATTTCCTTCCGCTTTAACCGCATCCTGACTGTTGGGCCCCAAGCCTTTGCCTACGCCCCGG

CCCTGCAGGTGTTGTGGCTCAATATTAACAGCCTGGTGTGGCTGGACAGGCAGGCACTGTGGAGGCTGCACAACCTGAC

AGAGCTGCGCCTGGACAACAACCTGCTGACCGACCTCTATCACAACTCCTTCATTGACCTCCACAGACTGCGCACCCTC

AACCTGCGCAACAACCGTGTCTCCGTCCTCTTCTCTGGTGTCTTCCAGGGGCTGGCTGAGCTGCAGACGCTGGATTTAG

GGGGCAACAACTTGCGCCACCTGACTGCACAGTCACTGCAGGGGCTGCCCAAACTGCGCAGGCTGTACCTGGACCGCAA

CAGATTGCTGGAGGTGAGCAGCACTGTGTTCGCCCCAGTGCAGGCTACCCTGGGGGTGCTGGACCTGCGGGCCAACAAC

CTGCAGTACATCTCACAGTGGCTGCGCAAGCCGCCACCCTTCCGCAACCTGAGCAGCCTGTACGACCTGAAGCTGCAGG

CGCAGCAGCCCTATGGACTGAAGATGCTGCCTCACTACTTCTTCCAGGGCTTGGTGAGGCTGCAGCAGCTGTCGCTGTC

ACAGAACATGCTGCGGTCCATCCCACCGGATGTCTTCGAGGACTTGGGCCAGCTGCGCTCCCTGGCATTGGCTGACAGC

AGCAATGGGCTGCATGACCTGCCTGACGGCATCTTCAGAAACCTGGGCAACCTGCGGTTCCTGGACCTGGAGAATGCAG

GGCTGCACTCGCTCACTCTGGAAGTCTTCGGCAATCTCAGCCGGCTGCAGGTGCTGCACTTGGCCAGAAACGAGCTGAA

GACCTTCAATGACAGCGTTGCCAGCCGGCTGTCCTCCTTGCGCTACCTGGACCTGCGCAAGTGTCCGCTCAGCTGCACC

TGTGACAACATGTGGCTGCAGGGCTGGCTGAACAACAGCCGTGTGCAGGTTGTCTACCCCTACAACTACACCTGTGGCT

CACAGCACAATGCCTACATCCACAGCTTTGACACACACGTCTGCTTCCTGGACCTGGGGCTCTATCTCTTTGCTGGGAC

TGCACCGGCAGTGCTGCTGCTGCTGGTGGTGCCGGTGGTGTACCACCGCGCCTACTGGAGGCTGAAGTACCACTGGTAC

CTTCTGCGGTGCTGGGTCAACCAGCGGTGGCGGCGGGAGGAAAAGTGCTACCTCTATGACAGCTTTGTGTCCTACAATT

CAGCTGATGAAAGTTGGGTGTTGCAGAAGCTGGTGCCTGAGCTGGAGCACGGTGCCTTCCGCCTCTGCTTGCACCACCG

CGACTTCCAGCCGGGCCGCAGCATCATTGACAACATTGTGGATGCTGTCTACAACAGCCGGAAGACGGTGTGCGTGGTG

AGCCGCAGCTACCTGCGCAGCGAGTGGTGCTCTCTAGAGGTGCAGTTGGCCAGCTACCGGCTGTTGGATGAGCGGCGTG

ACATCCTGGTACTGGTGCTGCTGGAGGACGTGGGTGATGCTGAGCTGTCTGCCTACCACCGCATGCGGCGGGTGCTGCT

GCGGCGCACCTACCTGCGCTGGCCTCTTGACCCCGCAGCTCAGCCGCTCTTTTGGGCACGGCTGAAGAGGGCACTGAGG

TGGGGAGAGGGAGGAGAGGAGGAGGAAGAAGAAGGTTTGGGTGGAGGGACGGGAAGGCCCAGGGAAGGAGACAAACAGA

TGTAGCGGCCGC
```

Transfection of HEK293-pNifTy2-Zeo (Clonal Cell Line) with pcDNA3.1(+)-Neo-chiTLR21

Human embryonic kidney (HEK) cells 293 have been generated in the 1970s by viral transformation (Graham et al., 1977), and are now available to the research community via cell line repositories, such as ATCC.

pNifty2 is a plasmid that allows the detection of NFκB transcription factor activation, which is a hallmark of many immunostimulatory actions, toll-like receptor activations amongst them. The reporter gene in pNifTy2 dependent in its transcription/translation on NFκB activation is secreted alkaline phosphatase (SEAP). Details are described in the datasheet of the company selling this plasmid: Invivogen. Transformation/transfection events by pNifty2 are selected in both bacteria and mammalian cells by zeocin addition to the growth media.

HEK293 cells were transfected with pNifty2 by standard methods (lipofection), a stable cell line was selected, the functionality of the NF-κB/SEAP axis established by stimulation with human tumour necrosis factor α (Sigma). Secreted SEAP in the culture supernatant of stimulated cells was determined by a microtiter plate colorimetric assay employing the chromogenic substrate p-nitrophenylphosphate (pNPP, 5 mM) in an alkaline buffer (50 mM NaHCO$_3$, pH9.6, 2 mM MgCl$_2$). Colour development ($\lambda$=405 nm) was monitored by a microtiter plate reader. This readout was also used for selecting clonal lines (by the limiting dilution method) with high signal to noise ratios. One of these selected clones (dubbed clone 11) was then used for further studies with chicken TLR21.

pcDNA3.1(+)-neo is a standard mammalian expression vector purchased from Invitrogen. Subcloning of the chicken TLR21 gene into this vector was done via flanking Hind III (start codon) and Not I (stop codon) sites that were introduced by PCR. (See FIG. 1).

This plasmid was then transfected (lipofection) into the clonal HEK293-pNifty2-zeo line, and recombinant cells were selected by addition of both zeocin and G418 into the growth medium. Functionality of the resulting polyclonal recombinant cell line was assessed by stimulation of the culture with ODN-X4 and ODN-HEK1-PTO and detection of SEAP. Superior clonal lines were then identified by the limiting dilution method followed by stimulation and SEAP detection.

SEAP is a reporter enzyme in mammalian systems (Yang et al., 1997). SEAP is a secreted form of human embryonic alkaline phosphatase. Its main advantages are the high stability and the extremely high specific activity, which ensure sensitivity and robustness of detection. Several substrates have been described for SEAP detection, but the economical and robust pNPP was selected, as its reaction product p-nitrophenolate is detected with high sensitivity ($\epsilon_{405}$=18500 $M^{-1}$ $cm^{-1}$). In our test setups, we perform kinetic assays, because they provide a wider dynamic range of quantification.

HEK293-pNifTy2-Zeo cells were transfected with pcDNA3.1(+)-Neo-chiTLR21 (linearized with Pvu I) and a polyclonal cell line was selected by supplementing the media with 350 µg/ml zeocin and 600 µg/ml G418. A functionality test was performed by stimulating the cells with ODN-X4 (PDE) and with ODN-HEK1 (PTO). Secreted alkaline phosphatase (SEAP) was produced by the selected cells, but not by the parental HEK293-pNifTy2-Zeo cell line. Single cell cloning was performed and individual clones were analyzed for their responsiveness to ODN-X4 (PDE) (GGGGGGT-TCGTTTTCGTTTTCGTTGGGGG) (SEQ ID NO.:20) and ODN-HEK1 (PTO) (TCGTCGTTTTGTCGTTTGTCGTT) (SEQ ID NO.:21).

Out of 46 zeo/G418-double-resistant clonal cell lines, only 3 were clearly responsive to the ODN stimuli, while 3-4 further cell lines showed weaker signals. 85% of the selected clones were, therefore, not functional.

For all further studies, clonal cell line 38, which produced by far the highest SEAP readout signal on response to ODN-X4 (PDE) and ODN-HEK1 (PTO) stimulation, was used.

FIGS. 2-5 give an overview of the SEAP activity of the various zeo/G418-double-resistant clonal cell lines.

Example 2

In this homopolymer series based on the motif $^5{}'[G]_x$ {T C G T C G}$_n$ T C G [G]$_z{}^{3'}$ the 3'-dG run was shortened to one G for all ODNs tested.

E.g.: example X23N-5 represents [G]$_x$ {T C G T C G}$_n$ T C G [G]$_z{}^{3'}$ wherein x=7, z=0 and n=2: G$_7$ {T C G T C G}$_2$ T C G E.g.: example X23N-7 represents [G]$_x$ {T C G T C G}$_n$ T C G [G]$_z{}^{3'}$ wherein x=7, z=0 and n=3: G$_7$ {T C G T C G}$_3$ T C G

```
X23N-5    GGGGGGGTCGTCGTCGTCGTCG (SEQ ID NO.: 4)

X23N-7    GGGGGGGTCGTCGTCGTCGTCGTCG (SEQ ID
          NO.: 5)

X23N-9    GGGGGGGTCGTCGTCGTCGTCGTCGTCG
          (SEQ ID NO.: 6)

X23N-11   GGGGGGGTCGTCGTCGTCGTCGTCGTCGTCGTCG
          (SEQ ID NO.: 7)

X23N-13   GGGGGGGTCGTCGTCGTCGTCGTCGTCGTCGTCGTCG
          TCG (SEQ ID NO.: 8)

X23N-15   GGGGGGGTCGTCGTCGTCGTCGTCGTCGTCGTCGTCG
          TCGTCGTCG (SEQ ID NO.: 9)

X23N-17   GGGGGGGTCGTCGTCGTCGTCGTCGTCGTCGTCGTCG
          TCGTCGTCGTCG (SEQ ID NO.: 10)

X23N-19   GGGGGGGTCGTCGTCGTCGTCGTCGTCGTCGTCGTCG
          TCGTCGTCGTCGTCGTCG ((SEQ ID NO.: 11)

X23N-21   GGGGGGGTCGTCGTCGTCGTCGTCGTCGTCGTCGTCG
          TCGTCGTCGTCGTCGTCGTCGTCG (SEQ ID
          NO.: 12)

X23N-23   GGGGGGGTCGTCGTCGTCGTCGTCGTCGTCGTCGTCG
          TCGTCGTCGTCGTCGTCGTCGTCGTCGTCG (SEQ ID
          NO.: (13)

X23N-25   GGGGGGGTCGTCGTCGTCGTCGTCGTCGTCGTCGTCG
          TCGTCGTCGTCGTCGTCGTCGTCGTCGTCGTCGTCG
          (SEQ ID NO.: 14)

X23N-27   GGGGGGGTCGTCGTCGTCGTCGTCGTCGTCGTCGTCG
          TCGTCGTCGTCGTCGTCGTCGTCGTCGTCGTCGTCGT
          CG (SEQ ID NO.: 15)
```

Figure 6:
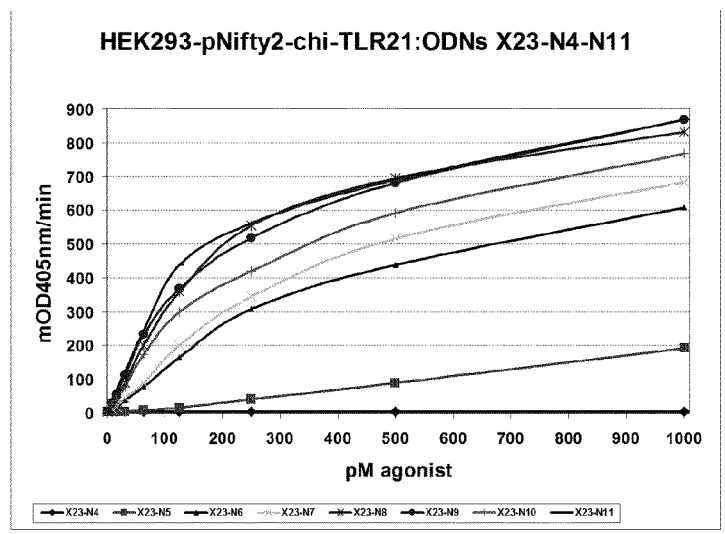
Figure 7:
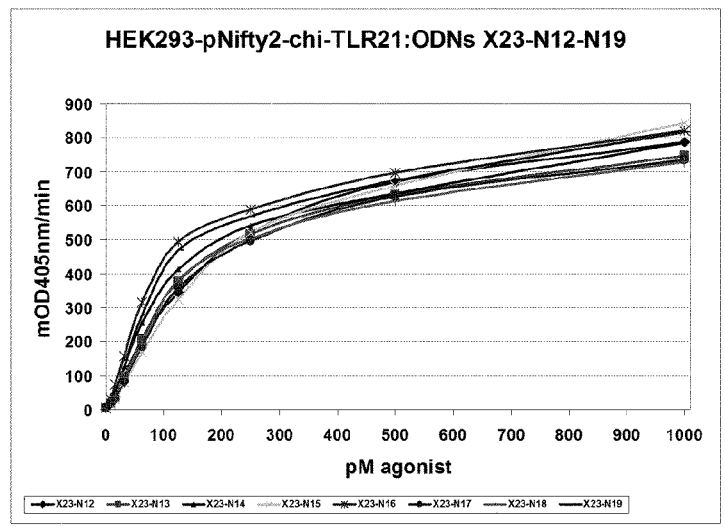
Figure 8:
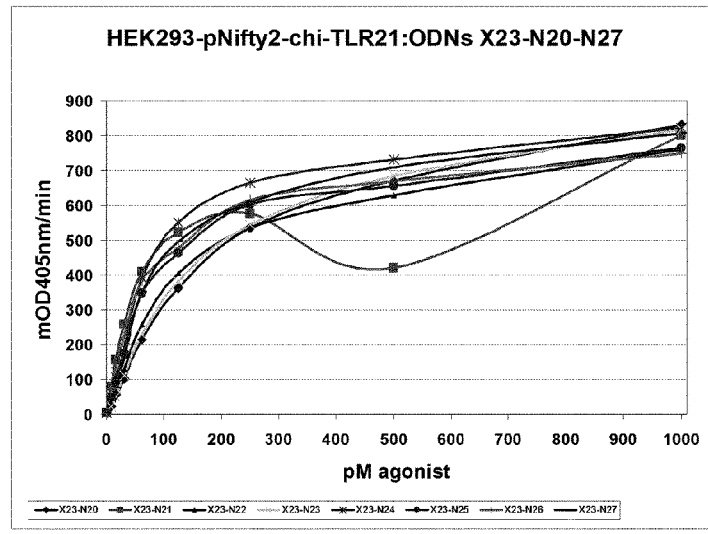

FIGS. 6-8 show the effect of X23-4 to X23N-27 in inducing an amount of the colored product absorbing at 405 nm of the reporter enzyme SEAP in the reporter cells HEK293-pNifty2-chickenTLR21.

Surprisingly, it can be concluded from FIG. 6, that already if n=3, the immuno-stimulatory effect is unexpectedly high. This effect is clearly quantified in an unexpectedly low $EC_{50}$ value in FIG. 9 (vide infra).

Furthermore, it can be concluded from FIGS. 6-8, that an increase from n=3 to n=13 gives an even further increase in activity (=a decrease in EC50). This increase shows a rather fast leveling off, once n reaches the value of 5.

Figure 9:
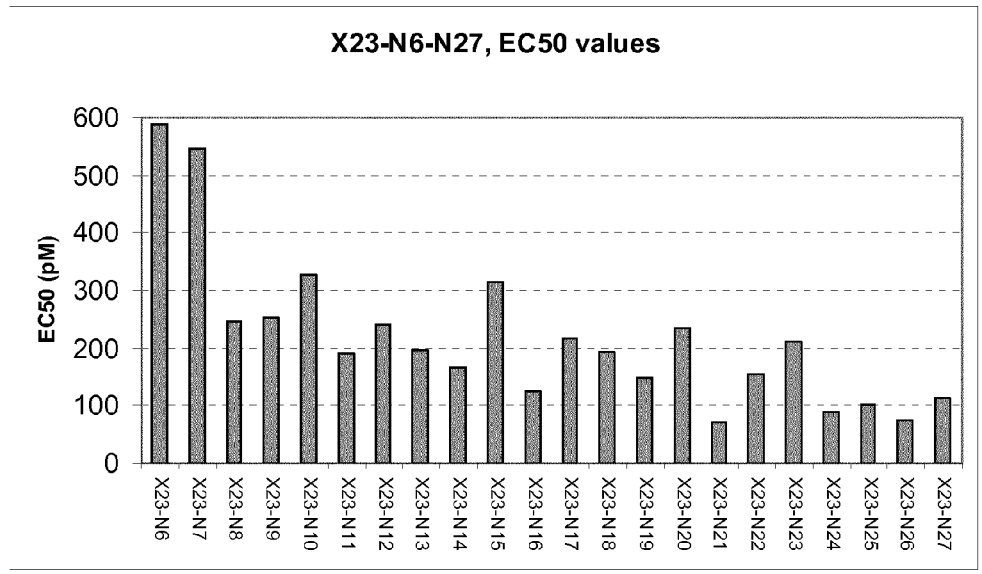

FIG. 9 shows the $EC_{50}$ value of X23-4 to X23N-27 in picomoles.

As can be seen from FIG. 9, already at a value of n=4, the $EC_{50}$ is only slightly above 200 pM, whereas from a value of n=10 onwards the $EC_{50}$ value reaches a plateau of slightly under 100 pM.

Example 3

In this homopolymer series based on the motif $^5{}'[G]_x$ {T C G T C G}$_n$ T C G [G]$_x{}^{3'}$ the number of 3'-G's was modified while n=4.

The following constructs were tested:

```
X23-six       5'-GGGGGGTCGTCGTCGTCGTCGTCGGGGG-3'
              (SEQ ID NO.: 16)

X23-six       5'-GGGGGGTCGTCGTCGTCGTCGTCGGGGGG-3'
              (SEQ ID NO.: 17)
(=X23, standard 1)

X4-pent       5'-GGGGGGTTCGTTTTCGTTTTCGTTTTCGTTT
              TCGTTGGGGG-3' (SEQ ID NO.: 18)
(=standard 2)

X23-nine-3455 5'-GGGGGTCGTCGTCGTCGTCGTCGTCGTC
              GGGGG-3' (SEQ ID NO.: 19)
(→ n = 4, x = 5, z = 4)

X23-nine-3451 5'-GGGGGTCGTCGTCGTCGTCGTCGTCGTC
              G-3' (SEQ ID NO.: 19)
(→ n = 4, x = 5, z = 0)
```

Figure 10:
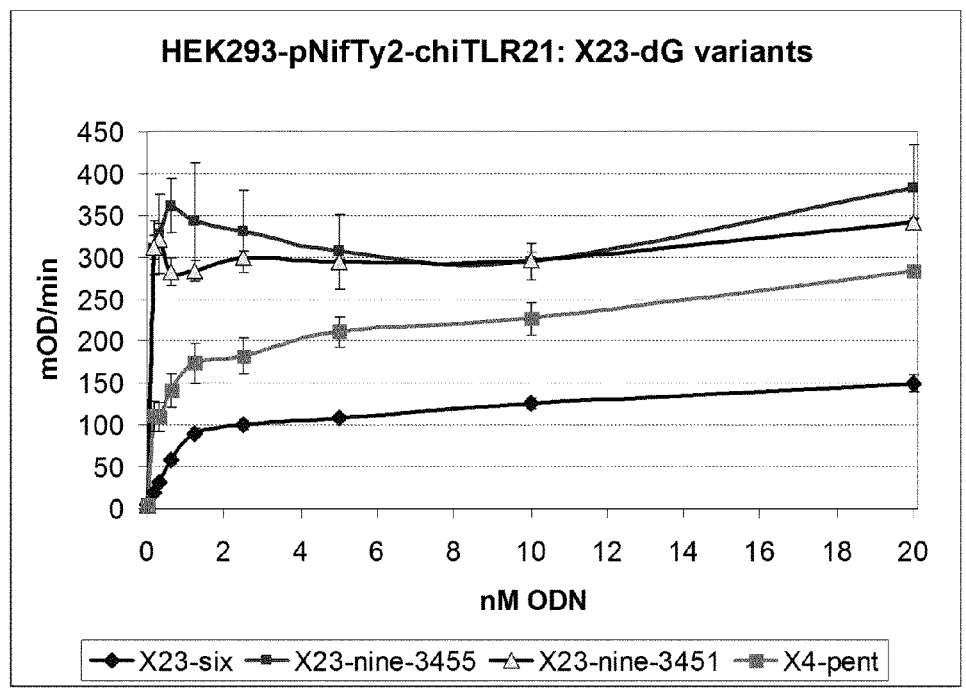

FIG. 10 shows the effect of changing the number of the 3'-G's in inducing an amount of the colored product absorbing at 405 nm of the reporter enzyme SEAP in the reporter cells HEK293-pNifty2-chickenTLR21.

The $EC_{50}$ for these CpG motifs is as follows:

| | |
|---|---|
| X4-pent (standard control) | 340 pM |
| X23-nine-3455 (n = 4, x = 5, z = 4) | <<100 pM |
| X23-nine-3451 (n = 4, x = 5, z = 0) | <<100 pM |

From this it can be derived that the number of 3'-G's is not particularly relevant provided that z=4 or less than 4, with regard to the $EC_{50}$.

LEGEND TO THE FIGURES

FIG. 1: Plasmid map of pcDNA3.1(+)-chiTLR21

FIG. 2-5: overview of the SEAP activity of the various zeo/G418-double-resistant clonal cell lines.

FIG. 6-8: these figures show the effect of X23-4 to X23N-27 in inducing an amount of the colored product absorbing at 405 nm of the reporter enzyme SEAP in the reporter cells (HEK293-pNifty2-chickenTLR21)

FIG. 9: this figure shows the $EC_{50}$ value of X23-4 to X23N-27 in picomoles.

FIG. 10: this figure shows the $EC_{50}$ values of X4-pent (standard control), X23-six, X23-nine-3455 and X23-nine-3451.

LITERATURE REFERENCES

Babiuk L. A., Gomis S., Hecker R., 2003. Molecular approaches to disease control. *Poult. Sci.* 82, 870-875.

Brownlie, R., Zhu J., Allan B., Mutwiri G. K., Babiuk L. A., Potter A., Griebel P., 2009. Chicken TLR21 acts as a functional homologue to mammalian TLR9 in the recognition of CpG oligodeoxynucleotides. *Mol. Immunol.* 46, 3163-3170

Carrington A. C., Secombes C. J., 2006. A review of CpGs and their relevance to aquaculture. *Vet. Immunol. Immunopathol.* 112, 87-101.

Daubenberger C. A., 2007. TLR9 agonists as adjuvants for prophylactic and therapeutic vaccines. *Curr. Opin. Mol. Ther.* 9, 45-52.

Dorn A., Kippenberger S., 2008. Clinical application of CpG-, non-CpG-, and antisense oligodeoxynucleotides as immunomodulators. *Curr. Opin. Mol. Ther.* 10, 10-20.

Fonseca D. E., Kline J. N., 2009. Use of CpG oligodeoxynucleotides in treatment of asthma and allergic disease. *Adv. Drug Deliv. Rev.* 61, 256-262.

Graham, F. L., Smiley, J., Russell, W. C., Nairn, R., 1977. Characteristics of a human cell line transformed by DNA from human adenovirus type 5. *J. Gen. Virol.* 36, 59-74.

Griebel P. J., Brownlie R., Manuja A., Nichani A., Mookherjee N., Popowych Y., Mutwiri G., Hecker R., Babiuk L. A., 2005. Bovine toll-like receptor 9: a comparative analysis of molecular structure, function and expression. *Vet. Immunol. Immunopathol.* 108, 11-16.

Hemmi H, Takeuchi O., Kawai T., Kaisho T., Sato S., Sanjo H., Matsumoto M., Hoshino K., Wagner H., Takeda K., Akira S., 2000. A Toll-like receptor recognizes bacterial DNA. *Nature* 408, 740-745.

Iwasaki A, Medzhitov R. Regulation of adaptive immunity by the innate immune system. 2010. *Science* 327, 291-295.

Keestra A. M., 2008. Molecular dissection of the chicken Toll-like receptor repertoire. PhD thesis (Proefschrift), University of Utrecht, The Netherlands Kline J. N., 2007. Immunotherapy of asthma using CpG oligodeoxynucleotides. *Immunol. Res.* 39, 279-286.

Kline J. N., Krieg A. M., 2008. Toll-like receptor 9 activation with CpG oligodeoxynucleotides for asthma therapy. *Drug News Perspect.* 21, 434-439.

Klinman D. M., 2004. Immunotherapeutic uses of CpG oligodeoxynucleotides. *Nat. Rev. Immunol.* 4, 249-258.

Klinman D. M, Currie D., Gursel I., Verthelyi D., 2004. Use of CpG oligodeoxynucleotides as immune adjuvants. *Immunol. Rev.* 199, 201-216.

Klinman D. M., 2006. Adjuvant activity of CpG oligodeoxynucleotides. *Int. Rev. Immunol.* 25, 135-154.

Klinman D. M., Klaschik S., Sato T., Tross D., 2009. CpG oligodeoxynucleotides as adjuvants for vaccines targeting infectious diseases. *Adv. Drug Deliv. Rev.* 61, 248-255.

Kindrachuk J., Potter J., Wilson H. L., Griebel P., Babiuk L. A., Napper S., 2008. Activation and regulation of toll-like receptor 9: CpGs and beyond. *Mini Rev. Med. Chem.* 8, 590-600.

Krieg A. M., Yi A, K., Matson S, Waldschmidt T, J., Bishop G. A., Teasdale R., Koretzky G. A., Klinman D. M., 1995. CpG motifs in bacterial DNA trigger direct B-cell activation. *Nature* 374, 546-549.

Krieg A. M., 2002. CpG motifs in bacterial DNA and their immune effects. *Annu. Rev. Immunol.* 20, 709-760.

Krieg A. M., 2003. CpG motifs: the active ingredient in bacterial extracts? *Nat. Med.* 9, 831-835.

Krieg A. M., 2006. Therapeutic potential of Toll-like receptor 9 activation. *Nat. Rev. Drug Discov.* 5, 471-484.

Krieg A. M., 2007a. Anti-infective applications of toll-like receptor 9 agonists. *Proc. Am. Thorac. Soc.* 4, 289-294.

Krieg A. M., 2007b. Development of TLR9 agonists for cancer therapy. *J. Clin. Invest.* 117, 1184-1194.

Linghua Zhang et al., 2007. Vaccination with Newcatle disease vaccine and CpG oligodeoxynucleotides induces specific immunity and protection against Newcastle disease virus in SPF chicken. *Vet. Immun. And Immunopath.* 115, 216-222.

Medzhitov R., 2001. CpG DNA: security code for host defense. *Nat. Immunol.* 2, 15-16.

Medzhitov R., Approaching the asymptote: 20 years later. 2009. *Immunity* 30, 766-775)

Mutwiri G., van Drunen Littel-van den Hurk S., Babiuk L. A., 2009. Approaches to enhancing immune responses stimulated by CpG oligodeoxynucleotides. *Adv. Drug Deliv. Rev.* 61, 226-232.

Mutwiri G., Pontarollo R., Babiuk S., Griebel P., van Drunen Littel-van den Hurk S., Mena A., Tsang C., Alcon V., Nichani A., Ioannou X., Gomis S., Townsend H., Hecker R., Potter A., Babiuk L. A., 2003. Biological activity of immunostimulatory CpG DNA motifs in domestic animals. Vet. Immunol Immunopathol. 91, 89-103.

Schindler, U., and Baichwal, V. R., 1994. Moll. Cell. Biol. 14: 5820-5831.

Singh M., O'Hagan D. T., 2003. Recent advances in veterinary vaccine adjuvants. *Int. J. Parasitol.* 33, 469-478.

Vollmer J., 2005. Progress in drug development of immunostimulatory CpG oligodeoxynucleotide ligands for TLR9. *Expert Opin. Biol. Ther.* 5, 673-682.

Vollmer J., Krieg A. M., 2009 Immunotherapeutic applications of CpG oligodeoxynucleotide TLR9 agonists. *Adv. Drug Deliv. Rev.* 61, 195-204.

Wagner H., 2009. The immunogenicity of CpG-antigen conjugates. *Adv. Drug. Deliv. Rev.* 61, 243-247.

Weiner G. J., 2009. CpG oligodeoxynucleotide-based therapy of lymphoid malignancies. *Adv. Drug Deliv. Rev.* 61, 263-267.

Werling D., Jungi T. W., 2003. TOLL-like receptors linking innate and adaptive immune response. *Vet. Immunol. Immunopathol.* 91, 1-12.

Wilson H. L., Dar A., Napper S. K., Marianela Lopez A., Babiuk L. A., Mutwiri G. K., 2006. Immune mechanisms and therapeutic potential of CpG oligodeoxynucleotides. *Int. Rev. Immunol.* 25, 183-213.

Wilson K. D., de Jong S. D., Tam Y. K., 2009. Lipid-based delivery of CpG oligodeoxynucleotides enhances immunotherapeutic efficacy. *Adv. Drug Deliv. Rev.* 61, 233-242.

Yang, T. T., Sinai, P., Kitts, P. A., Kain, S. R., 1997. Quantification of gene expression with a secreted alkaline phosphatase reporter system. *Biotechniques* 23, 1110-1114.

---

The invention claimed is:

1. An immunostimulatory non-methylated oligodeoxynucleotide having the general formula $$5' [G]_x \{T C G T C G\}_n T C G [G]_z 3'$$

wherein
x=3-20;
z=0-10;
n=4-18;
or a pharmaceutically acceptable salt thereof;
wherein when said immunostimulatory non-methylated oligodeoxynucleotide is administered to a chicken, it stimulates the initiation of signaling cascades leading to the activation of transcription factors that in turn result in the expression of inflammatory cytokines.

2. An immunostimulatory non-methylated oligodeoxynucleotide according to claim 1, characterised in that
x=3-10;
z<5.

3. The oligodeoxynucleotide according to claim 1, wherein the $^{5'} [G]_x$ and the $^{3'} [G]_z$ nucleotides have a phosphorothioate binding and the other nucleotides have a phosphodiester binding.

4. The oligodeoxynucleotide according to claim 1, wherein said oligodeoxynucleotide is coupled to a carrier or hapten.

5. A vector comprising the oligodeoxynucleotide according to claim 1.

6. A vaccine for preventing or combating an infectious disease, characterised in that said vaccine comprises an immunostimulatory amount of an oligodeoxynucleotide according to claim 1, an immunogenic amount of an antigen component or genetic information encoding an antigen component, and a pharmaceutically acceptable carrier.

7. A vaccine for preventing or combating an infectious disease, characterised in that said vaccine comprises an immunostimulatory amount of an oligodeoxynucleotide according to claim 1, an immunogenic amount of an antigen component or genetic information encoding an antigen component, and a pharmaceutically acceptable carrier, wherein said antigen component is, or is derived from a virus or micro-organism that in its wild-type form is pathogenic to poultry.

8. A vaccine for preventing or combating an infectious disease, characterised in that said vaccine comprises an immunostimulatory amount of an oligodeoxynucleotide according to claim 1, an immunogenic amount of an antigen component or genetic information encoding an antigen component, and a pharmaceutically acceptable carrier, wherein said antigen component is, or is derived from a virus or micro-organism that in its wild-type form is pathogenic to poultry, and wherein said virus or micro-organism is selected from the group consisting of Infectious Bronchitis virus, Newcastle Disease virus, Infectious Bursal Disease (Gumboro), Chicken Anaemia agent, Avian Reovirus, *Mycoplasma gallisepticum*, Turkey Rhinotracheitis virus, *Haemophilus paragallinarum* (Coryza), Chicken Poxvirus, Avian Encephalomyelitis virus, Egg Drop syndrome virus, Infectious Laryngotracheitis virus, Herpesvirus of Turkeys, *Eimeria* species, *Ornithobacterium rhinotracheale, Pasteurella multocida, Mycoplasma synoviae, Salmonella* species and *E. coli*.

9. A vaccine for preventing or combating an infectious disease, characterised in that said vaccine comprises a vector comprising the oligodeoxynucleotide according to claim 1, an immunogenic amount of an antigen component or genetic information encoding an antigen component, and a pharmaceutically acceptable carrier.

10. A vaccine for preventing or combating an infectious disease, characterised in that said vaccine comprises a vector comprising the oligodeoxynucleotide according to claim 1, an immunogenic amount of an antigen component or genetic information encoding an antigen component, and a pharmaceutically acceptable carrier, wherein said antigen component is, or is derived from a virus or micro-organism that in its wild-type form is pathogenic to poultry.

11. A vaccine for preventing or combating an infectious disease, characterised in that said vaccine comprises a vector comprising the oligodeoxynucleotide according to claim 1, an immunogenic amount of an antigen component or genetic information encoding an antigen component, and a pharmaceutically acceptable carrier, wherein said antigen component is, or is derived from a virus or micro-organism that in its wild-type form is pathogenic to poultry, and wherein said virus or micro-organism is selected from the group consisting of Infectious Bronchitis virus, Newcastle Disease virus, Infectious Bursal Disease (Gumboro), Chicken Anaemia agent, Avian Reovirus, *Mycoplasma gallisepticum*, Turkey Rhinotracheitis virus, *Haemophilus paragallinarum* (Coryza), Chicken Poxvirus, Avian Encephalomyelitis virus, Egg Drop syndrome virus, Infectious Laryngotracheitis virus, Herpesvirus of Turkeys, *Eimeria* species, *Ornithobacterium rhinotracheale, Pasteurella multocida, Mycoplasma synoviae, Salmonella* species and *E. coli*.

12. A medicament comprising an immune stimulating amount of a vector comprising the oligodeoxynucleotide of claim 1 and an immunogenic amount of an antigen component or genetic information encoding an antigen component.

13. A method of preventing or combating infectious disease in poultry comprising administrating the medicament of claim 12 to poultry.

\* \* \* \* \*